United States Patent
Lin et al.

(10) Patent No.: US 11,015,823 B2
(45) Date of Patent: May 25, 2021

(54) ELECTRONIC APPARATUS CAPABLE OF AIR POLLUTION REDUCTION

(71) Applicant: National Cheng Kung University, Tainan (TW)

(72) Inventors: Ming-Yeng Lin, Tainan (TW); Hong-Yiou Lin, Tainan (TW); How-Ran Guo, Tainan (TW); Huann-Shyang Lin, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 216 days.

(21) Appl. No.: 16/212,758

(22) Filed: Dec. 7, 2018

(65) Prior Publication Data

US 2019/0178510 A1 Jun. 13, 2019

Related U.S. Application Data

(60) Provisional application No. 62/596,122, filed on Dec. 8, 2017, provisional application No. 62/607,933, filed on Dec. 20, 2017.

(51) Int. Cl.
*A61C 1/00* (2006.01)
*A61C 3/02* (2006.01)
(Continued)

(52) U.S. Cl.
CPC ............ *F24F 8/10* (2021.01); *A61B 18/1402* (2013.01); *A61C 1/00* (2013.01); *A61C 3/02* (2013.01); *A61C 17/0208* (2013.01); *A61C 19/007* (2013.01); *A61L 9/015* (2013.01); *A61L 9/20* (2013.01); *A61L 9/22* (2013.01); *B01D 45/12* (2013.01); *B03C 3/019* (2013.01); *B03C 3/12* (2013.01); *B03C 3/155* (2013.01); *B03C 3/36* (2013.01); *B03C 3/38* (2013.01); *B03C 3/41* (2013.01); *F24F 8/192* (2021.01); *A61B 2218/008* (2013.01); *A61L 2209/111* (2013.01); *A61L 2209/12* (2013.01); *A61L 2209/134* (2013.01); *A61L 2209/14* (2013.01); *A61L 2209/212* (2013.01); *B03C 2201/04* (2013.01); *B03C 2201/26* (2013.01); *F24F 8/108* (2021.01); *F24F 8/22* (2021.01); *F24F 8/26* (2021.01); *F24F 8/40* (2021.01); *F24F 2110/65* (2018.01)

(58) Field of Classification Search
CPC ........... A61C 1/00; A61C 19/007; A61C 3/02; A61B 18/1402; A61L 9/22; F24F 3/1603; B03C 3/38; B03C 3/41; B03C 3/155
USPC ............................... 55/385.1; 606/34, 37, 84
See application file for complete search history.

(56) References Cited

U.S. PATENT DOCUMENTS

| 6,786,906 B1* | 9/2004 | Cobb | ...................... A61B 18/14 606/37 |
| 2002/0103485 A1* | 8/2002 | Melnyk | .................. A61B 18/14 606/45 |

(Continued)

FOREIGN PATENT DOCUMENTS

CN 104949196 A 9/2015

*Primary Examiner* — Minh Chau T Pham

(74) *Attorney, Agent, or Firm* — Bacon & Thomas, PLLC

(57) ABSTRACT

An electronic apparatus capable of air pollution reduction includes an operating tool and an airflow device. The airflow device is located adjacent to the operating tool, and has a shell with one or more opening holes distributed thereon for air to flow in or out.

19 Claims, 10 Drawing Sheets

(51) Int. Cl.

| | | |
|---|---|---|
| *A61L 9/22* | (2006.01) | |
| *B03C 3/38* | (2006.01) | |
| *B03C 3/41* | (2006.01) | |
| *B03C 3/155* | (2006.01) | |
| *F24F 8/10* | (2021.01) | |
| *B03C 3/019* | (2006.01) | |
| *B01D 45/12* | (2006.01) | |
| *B03C 3/12* | (2006.01) | |
| *B03C 3/36* | (2006.01) | |
| *A61L 9/20* | (2006.01) | |
| *A61B 18/14* | (2006.01) | |
| *A61L 9/015* | (2006.01) | |
| *A61C 19/00* | (2006.01) | |
| *A61C 17/02* | (2006.01) | |
| *F24F 8/192* | (2021.01) | |
| *F24F 110/65* | (2018.01) | |
| *F24F 8/22* | (2021.01) | |
| *F24F 8/26* | (2021.01) | |
| *F24F 8/40* | (2021.01) | |
| *F24F 8/108* | (2021.01) | |

(56) References Cited

U.S. PATENT DOCUMENTS

| | | | |
|---|---|---|---|
| 2008/0058821 A1* | 3/2008 | Maurer | A61B 18/1402 606/84 |
| 2011/0118733 A1* | 5/2011 | Liu | A61B 18/1477 606/42 |
| 2011/0295250 A1* | 12/2011 | Johnson | A61B 18/042 606/41 |
| 2015/0157390 A1* | 6/2015 | Fleenor | A61M 1/0039 606/34 |
| 2016/0278874 A1* | 9/2016 | Fleenor | A61B 18/1402 |
| 2017/0325886 A1* | 11/2017 | Graham | A61B 18/148 |
| 2019/0117858 A1* | 4/2019 | Wierzba | A61B 18/1206 |
| 2019/0159830 A1* | 5/2019 | Horner | A61B 18/1402 |
| 2019/0201593 A1* | 7/2019 | Shelton, IV | G05B 15/02 |
| 2019/0247141 A1* | 8/2019 | Batchelor | A61B 18/1402 |
| 2020/0093535 A1* | 3/2020 | Manley | A61B 18/1402 |

* cited by examiner

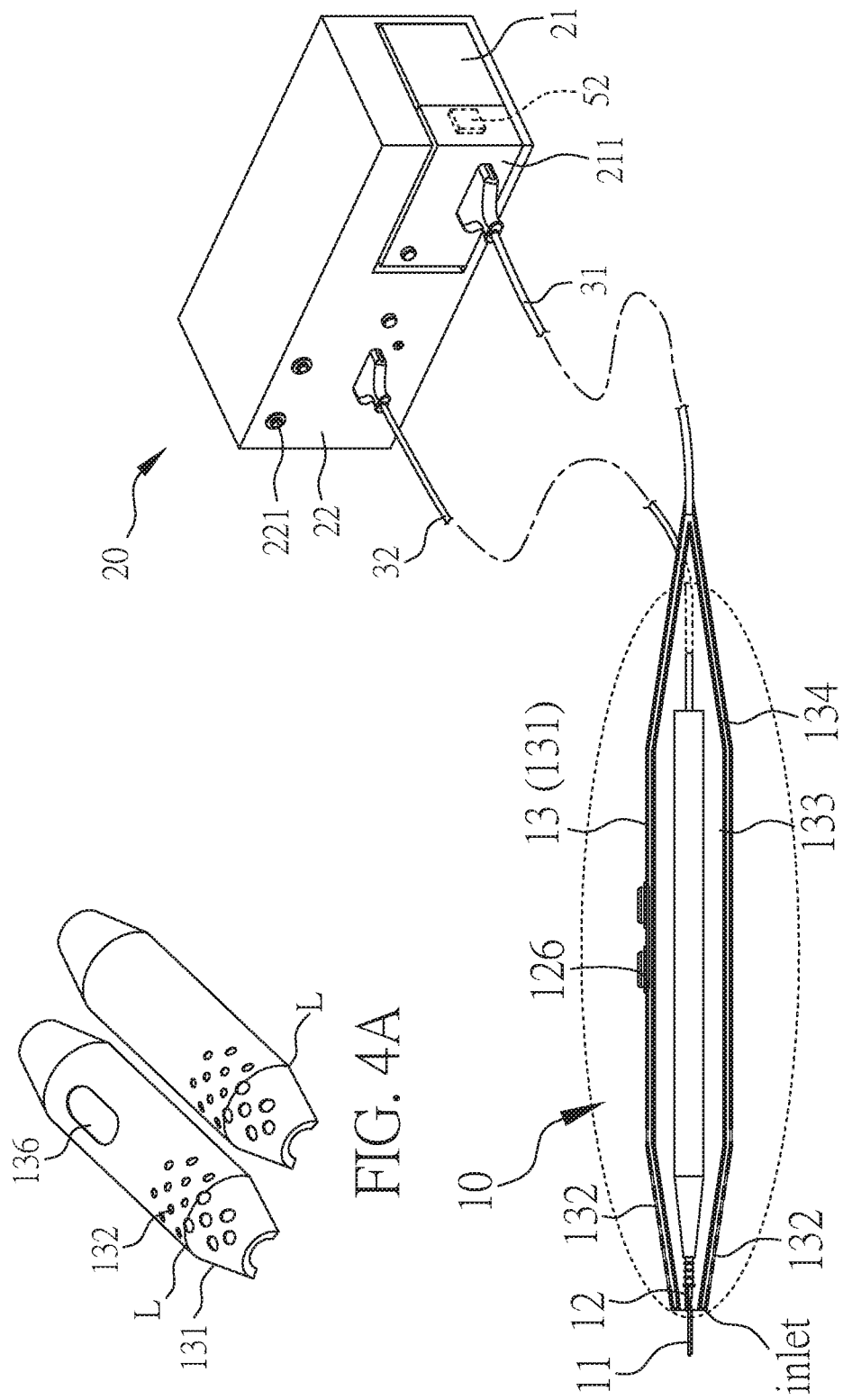

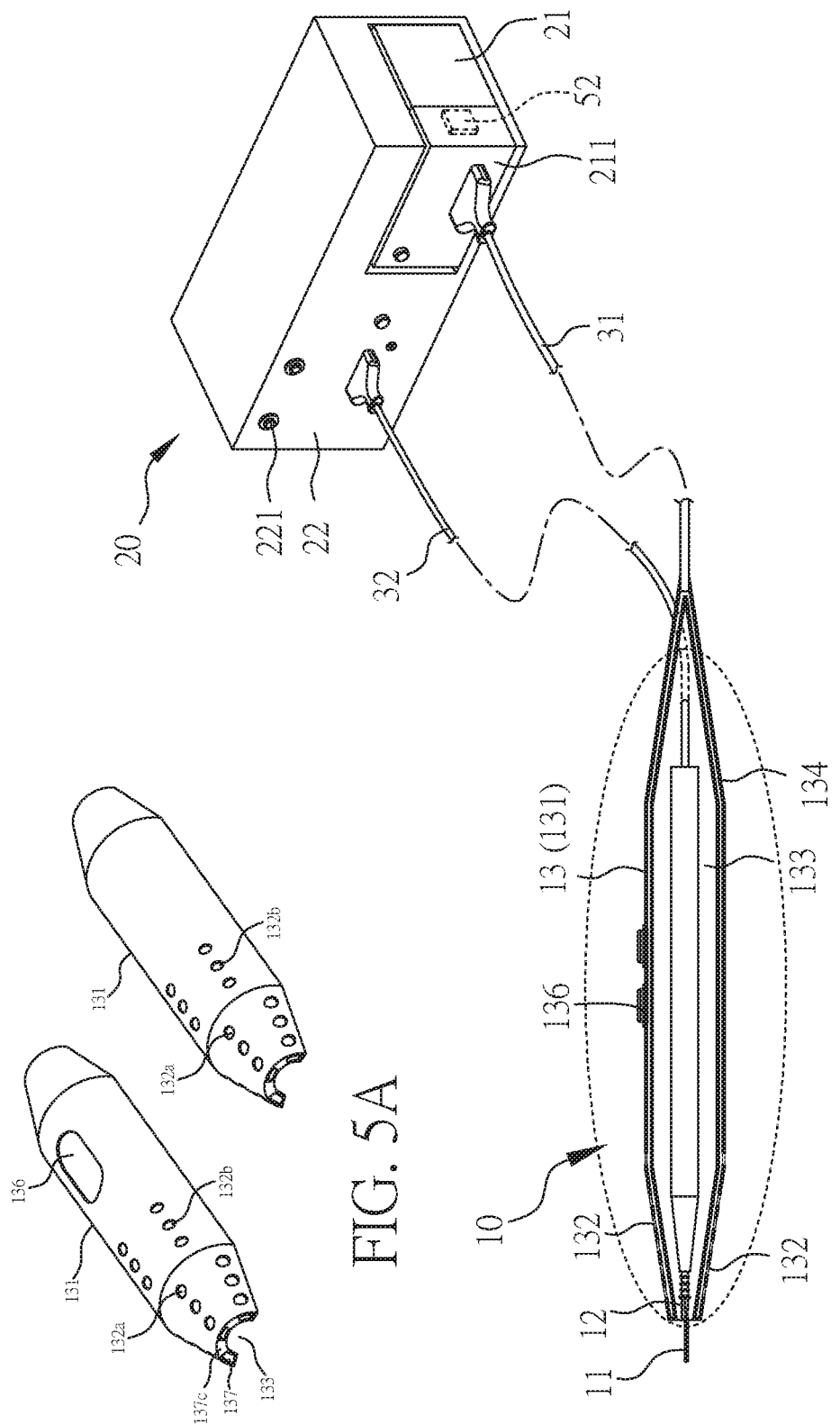

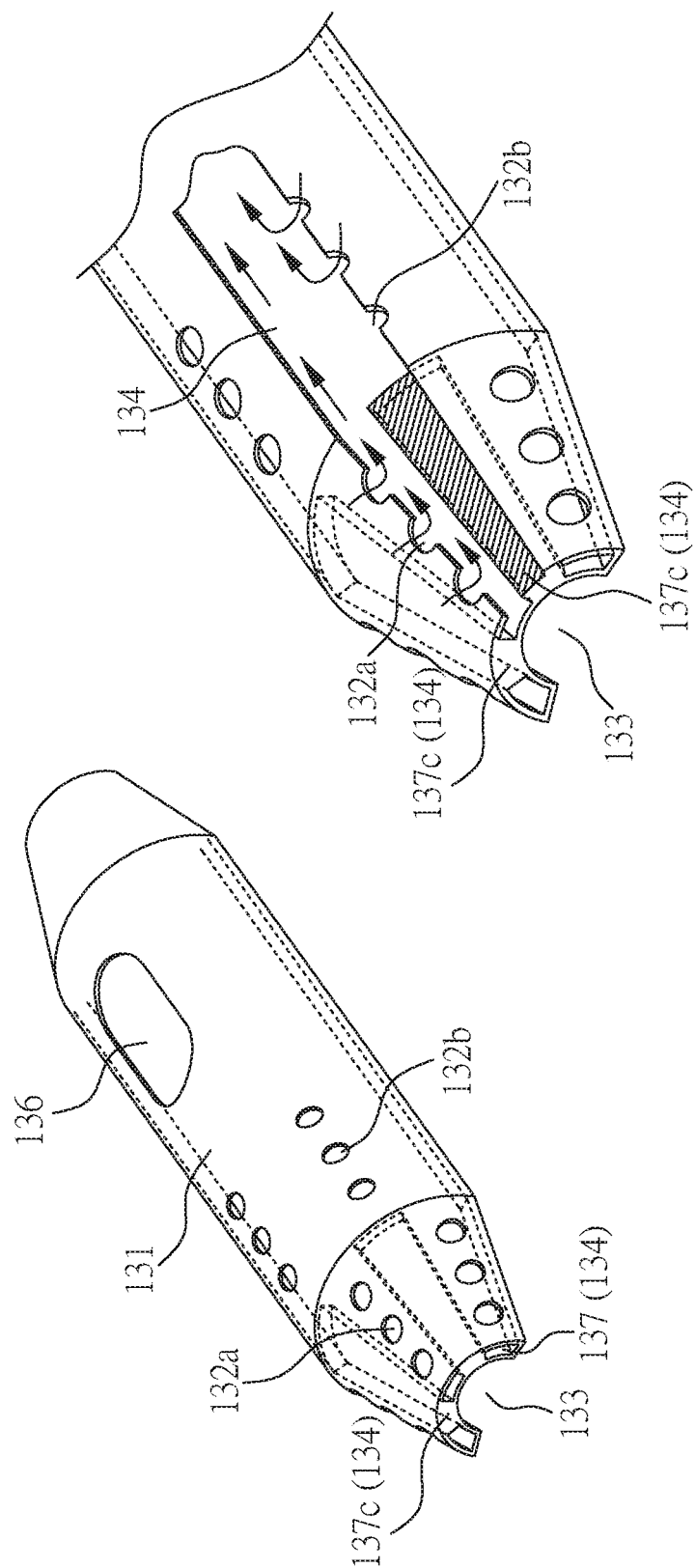

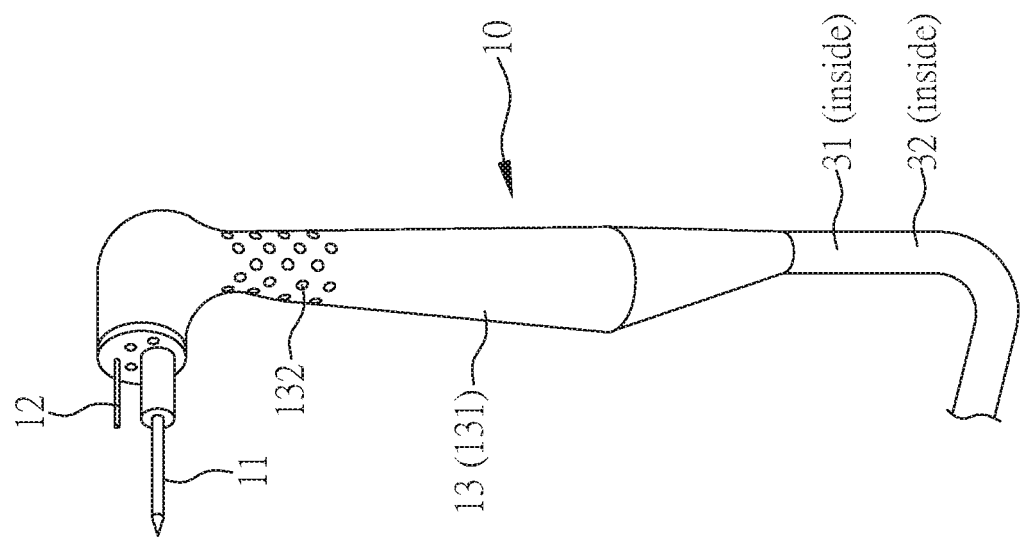

ELECTRONIC APPARATUS CAPABLE OF AIR POLLUTION REDUCTION

CROSS REFERENCE TO RELATED APPLICATION

This application claims the benefit of filing date of U.S. Provisional Application Ser. No. 62/596,122, entitled "ELECTRONIC DEVICE WITH AIR POLLUTION REDUCTION SYSTEM" filed Dec. 8, 2017 under 35 USC § 119(e)(1).

This application claims the benefit of filing date of U.S. Provisional Application Ser. No. 62/607,933, entitled "ELECTRONIC DEVICE WITH AIR POLLUTION REDUCTION SYSTEM" filed Dec. 20, 2017 under 35 USC § 119(e)(1).

BACKGROUND OF THE INVENTION

1. Field of the Invention

The present invention relates to an electronic apparatus with an airflow device which can be used in different workplaces, such as a surgery room, a dental office, or a welding factory.

2. Description of Related Art

Air pollution occurs when using an electronic device, such as an electrosurgical pencil in a surgery room, a dental drill in a dental office, or a welding torch in a welding factory.

In the case of the surgery room, an electrosurgical pencil is used to cut a biological tissue by heating the biological tissue with electrical current. Surgical smoke is being produced during a surgical process using the electrosurgical pencil. The surgical smoke contains hazardous materials, such as volatile organic compounds (VOCs), ultrafine particles, biological aerosols (bioaerosols), and so on. Researches have shown that the surgical smoke may cause headaches, allergies, or air transmitted diseases. In particular, surgeons or medical personnel participating in a surgery may be exposed to risks of respiratory diseases. Concerns therefore have been raised regarding toxicities of the surgical smoke produced by the electrosurgical pencil.

A convenient way to reduce the surgical smoke is to introduce a smoke evacuation device, which may be a standalone device, or equipped with the electrosurgical pencil.

A standalone smoke evacuation device is deemed to have a better performance for smoke removal. However, it is an individual instrument which has to be held by another person other than a surgeon, and thus more people may be exposed to air pollution.

For the smoke evacuation device equipped with the electrosurgical pencil, a smoke entrance of the smoke evacuation device is typically located close to a tip of the electrosurgical pencil for the sake of capturing the surgical smoke. However, such an evacuation device only has a single inlet and can only capture the surgical smoke in a small region, and cannot achieve favorable performance.

In the case of the dental office, bioaerosols or particles are emitted during a dental treatment using the dental drill. A current clinic simply uses a standalone suction to deal with the emitted materials. However, the standalone suction often blocks a view of a dentist, and thus affects the dental treatment. The standalone suction is not efficient enough to protect a healthcare worker. There is still a need to improve the air quality in the dental office.

In the case of the welding factory, a large amount of air pollution occurs during a welding process. Respiratory diseases, such as lung cancers, have been reported among welding workers. A local exhaust ventilation (LEV) is commonly employed in the welding factory to remove the air pollution. However, it sometimes obstructs a view of an operator.

Therefore, it is desirable to provide an improved electronic apparatus to mitigate and/or obviate the aforementioned problems.

SUMMARY OF THE INVENTION

One objective of the present invention is to provide an electronic apparatus capable of air pollution reduction, which is capable of efficiently removing air pollutants.

To achieve the objective, the electronic apparatus capable of air pollution reduction is designed to include an operating tool and an airflow device. The airflow device is located adjacent to the operating tool, and has a shell with one or more opening holes distributed thereon for air to flow in or out.

Typically, air pollution is generated during an operation of the operating tool.

Optionally or preferably, the operating tool is a hand-held tool or a machine-held tool.

Optionally or preferably, the operating tool is an electrosurgical pencil, an electrocautery, a laser surgical device, a dental drill, dental scalar tool, a prophy angle, a welding torch, or an air pollution generating device.

Optionally or preferably, the electronic apparatus capable of air pollution reduction further includes an ionizer located adjacent to the operating tool, and configured to emit charged ions, wherein the ionizer includes at least one point ionizer, at least one wire, and/or at least one ground plate.

Optionally or preferably, the electronic apparatus capable of air pollution reduction further includes an airflow generator connected to the airflow device, wherein the airflow generator is a vacuum pump configured to extract air from the airflow device, or an air blower configured to blow air into the airflow device.

Optionally or preferably, the airflow generator is equipped with a high efficiency particulate air (HEPA) filter, an ultra-low penetration air (ULPA) filter, a membrane filter, a nano-fiber filter, a carbon filter, a gas filter, a catalyst filter, or an anti-microbial filter.

Alternatively, the airflow generator is equipped with an ultraviolet air purifier with an ultraviolet light source to terminate a living organism.

Alternatively, the airflow generator is equipped with an ozone generator.

Alternatively, the airflow generator is equipped with an impactor.

Alternatively, the airflow generator is equipped with a cyclone.

Optionally or preferably, the electronic apparatus capable of air pollution reduction further includes a deposition surface having charges opposite to the charged ions, such as an electret filter.

Optionally or preferably, the electronic apparatus capable of air pollution reduction further includes a deposition surface formed of uncharged material adapted to capture particles charged by the charged ions.

Optionally or preferably, the electronic apparatus capable of air pollution reduction further includes a power supply connected to the operating tool, the ionizer, and/or the airflow device.

Optionally or preferably, the airflow generator and the power supply are integrated into an electrical power box.

Optionally or preferably, the electronic apparatus capable of air pollution reduction further includes a controller configured to control an ion generation rate of the ionizer, an airflow rate of the airflow generator, a power output of the power supply, or a deposition surface charge density of a deposition surface.

Optionally or preferably, the controller is configured to be controlled by a computer, a tablet, a plate panel, a smart phone, or a remote controller.

Optionally or preferably, the shell of the airflow device is an irremovable body wrapping around and integrated with the operating tool.

Alternatively, the shell of the airflow device is a removable body wrapping around the operating tool.

Alternatively, the shell of the airflow device is a removable body fixed to the operating tool.

Optionally or preferably, the shell of the airflow device includes a plurality of layers to form an innermost region and an outermost region wrapping around and isolated to the innermost region, the operating tool is located in the innermost region, and an air channel is formed in the outermost region.

Optionally or preferably, the shell of the airflow device includes a plurality of radial subsections isolated to each other, each radial subsection has a group of opening holes, and one group of opening holes is located before another group of opening holes along a longitudinal axis of the shell.

Optionally or preferably, at least one of the radial subsections has a sealed portion disconnected to the airflow generator, and located before the opening holes along the longitudinal axis of the shell.

Optionally or preferably, the shell of the airflow device includes a former portion having large opening holes, and a latter portion having small opening holes.

Optionally or preferably, the electronic apparatus capable of air pollution reduction includes an air pollution sensor located adjacent to the operating tool, configured to detect an air pollution concentration, and send a control signal to control any or all of an airflow rate of the airflow generator, a power output to the operating tool, a power supplied to the ionizer, or a deposition surface charge density of a deposition surface.

Optionally or preferably, the electronic apparatus capable of air pollution reduction includes a sensor or a switch configured to detect an operation of the operating tool, and generate a control signal to turn on the airflow device, an ionizer, and/or a deposition surface.

Other objectives, novel and inventive features, and their respective advantages of the present invention will become more apparent from the following detailed description when taken in conjunction with the accompanying drawings.

BRIEF DESCRIPTION OF THE DRAWINGS

FIGS. 4 and 4A are schematic diagrams illustrating the structure of the electronic apparatus capable of air pollution reduction according to a fourth embodiment of the present invention;

FIG. 5 is a schematic diagram illustrating the structure of the electronic apparatus capable of air pollution reduction according to a fifth embodiment of the present invention;

FIGS. 5A to 5C are schematic diagram illustrating the structure of the shell according to the fifth embodiment of the present invention; and FIG. 6 is a schematic diagram illustrating the structure of the electronic apparatus capable of air pollution reduction according to a sixth embodiment of the present invention.

DETAILED DESCRIPTION OF THE EMBODIMENTS

Various embodiments are provided in the following description for the purpose of illustrating the present invention, and are not meant to be limiting. The features and the functions of one embodiment may be applied to another embodiment by variation, modification, combination, separation, selection, or transformation in a suitable manner.

A figure may show essential elements and optional or preferable elements of one embodiment. In other words, it does not mean that all elements in the figure are essential elements of the embodiment.

First Embodiment

Figure 1:
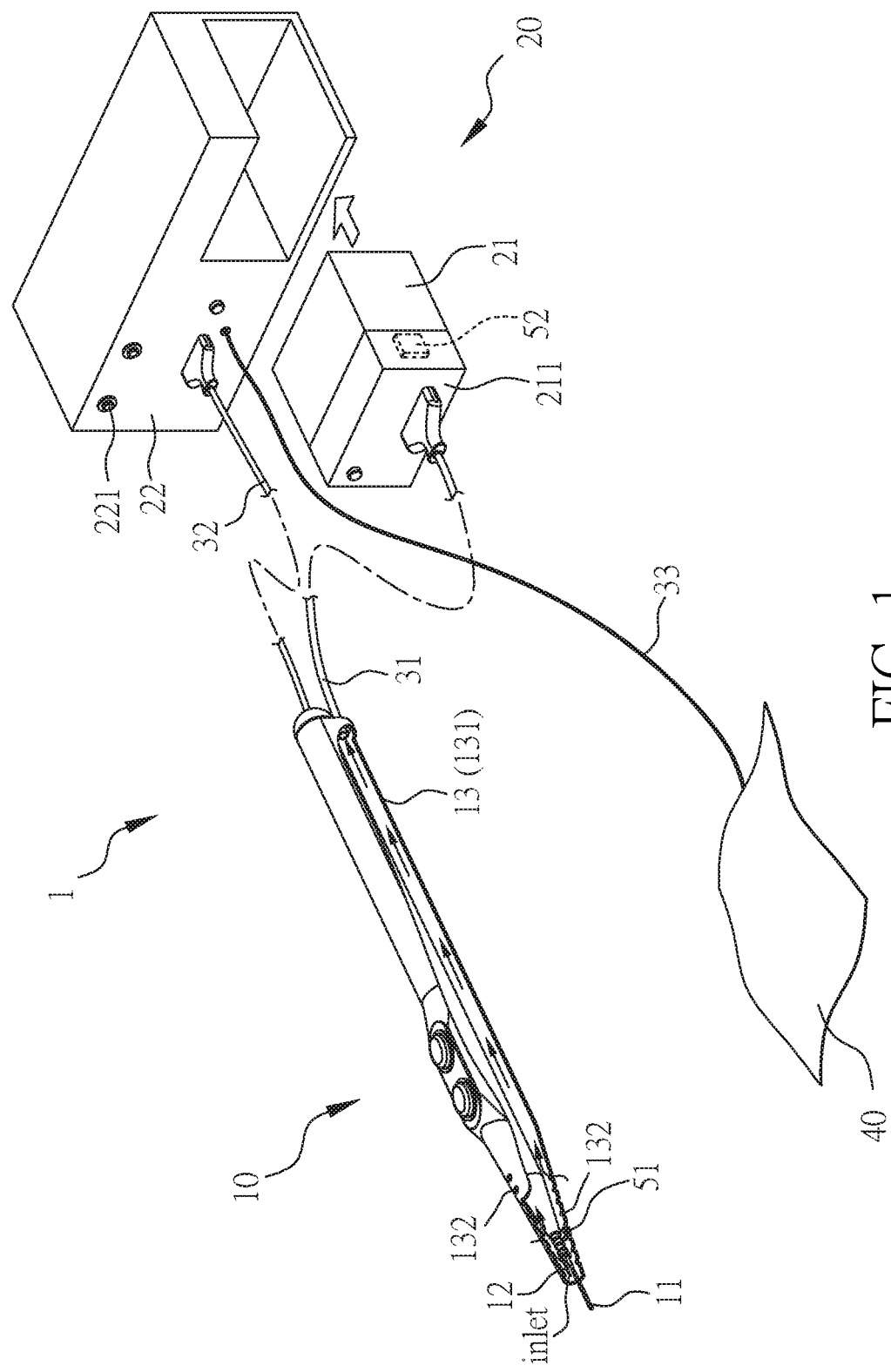
FIG. 1 is a schematic diagram illustrating the structure of the electronic apparatus capable of air pollution reduction according to a first embodiment of the present invention.

FIG. 1 is a schematic diagram illustrating the structure of the electronic apparatus capable of air pollution reduction 1 according to a first embodiment of the present invention.

In this embodiment, the electronic apparatus capable of air pollution reduction 1 is an electrosurgical apparatus. However, in other embodiments, it may be a dental apparatus or a welding apparatus, and is not limited thereto.

The electronic apparatus capable of air pollution reduction 1 includes two main units, an operating device 10 and an electrical power box 20.

Figure 1A:
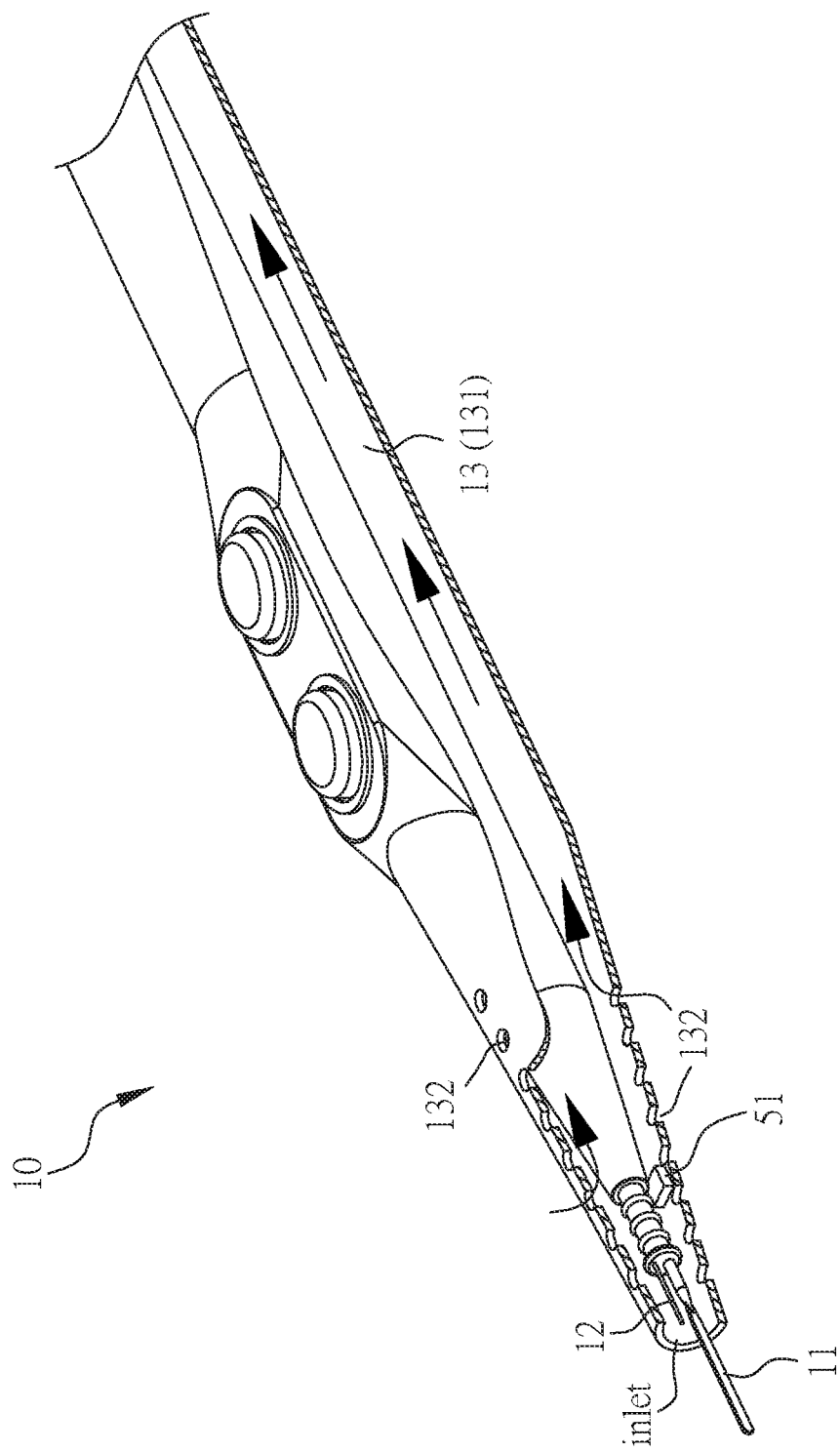
FIG. 1A is an enlarged view illustrating a portion of the operating device according to the first embodiment of the present invention.

FIG. 1A is an enlarged view illustrating a portion of the operating device 10 according to the first embodiment of the present invention.

The operating device 10 is typically portable. In this embodiment, the operating device 10 includes an operating tool 11, an ionizer 12, and an airflow device 13. However, in other embodiments, any of the operating tool 11, the ionizer 12, and the airflow device 13 may be separated from the operating device 10, and in other words, they are not necessary to be integrated into one unit.

The operating tool 11 may be a hand-held tool or a machine-held tool. In this embodiment, the operating tool 11 is an electrosurgical pencil having an electrode to cut an object (for example, a biological tissue). However, in other embodiments, the operating tool 11 may be an electrocautery, a laser surgical device, a dental drill, dental scalar tool, a prophy angle, or a welding torch, and is not limited thereto. Air pollution is generated during an operation of the operating tool 11. For example, surgical smoke is being produced during a surgical process of the electrosurgical pencil.

The ionizer 12 is located adjacent to the operating tool 11. In particular, an outlet (not labeled) of the ionizer 12 is adjacent to a tip of the operating tool 11. The ionizer 12 is configured to emit charged ions, especially a high concentration of charged ions, in order to reduce the concentration of air pollutants. As will be discussed later in the following description, the ionizer 12 may cooperate with a deposition surface 40 adapted to capture particles charged by the charged ions. The ionizer 12 may include at least one point ionizer, at least one wire, and/or at least one ground plate.

The airflow device 13 is located adjacent to the operating tool 11. The airflow device 13 has a shell 131 with one or more opening holes 132 (a plurality of opening holes are shown for example) distributed thereon for air to flow in or out. Typically, the opening holes 132 are distributed near an inlet of the shell 131, for the sake of evacuating the air pollutants generated by the operating tool 11, or blowing air in order to help the reduction of the air pollutants. The opening holes 132 may have different sizes or shapes. The airflow device 13 is adapted to be connected to an airflow generator 21, and an air channel (marked as arrows inside the airflow device 13) can be formed therebetween, as will be discussed in the following description.

To discuss in detail about the shell 131 of the airflow device 13, in this embodiment, the shell 131 is irremovable body wrapping around and integrated with the operating tool 11 (and the ionizer 12). However, in other embodiments, the shell 131 may be a removable body wrapping around the operating tool 11 or a removable body fixed to the operating tool 11, without modifying the structure of the operating tool 11. Anyway, the tip (not labeled) of the operating tool 11 has to protrude out of the shell 131 in order to contact a biological tissue, and the outlet (not labeled) of the ionizer 12 has to protrude out of the shell 131 in order to ionize air pollutants.

In this embodiment, the electrical power box 20 includes an airflow generator 21 and a power supply 22, and in other words, they are integrated (or assembled) therein. However, in other embodiments, the airflow generator 21 and the power supply 22 may be separated units. The airflow generator 21 may be powered by the power supply 22 or another dedicated power supply (now shown) for the airflow generator 21.

The airflow generator 21 may be a vacuum pump configured to extract air from the airflow device 13. The airflow generator 21 may also be an air blower configured to blow air into the airflow device 13. Typically, a laminar airflow is provided in a surgical room, pressing the air pollutants down to an exhaust, and the blown air may cooperate with the laminar airflow, helping the deposition of the air pollutants. In some embodiments, the airflow generator 21 may be switched between a vacuum pump function and an air blower function. The airflow generator 21 is connected to the airflow device 13 via an air pipe 31 between the operating device 10 and the electrical power box 20.

Moreover, the airflow generator 21 may be equipped with a functional component 211, and thus form an air cleaner. The functional component 211 may be a filter, such as a high efficiency particulate air (HEPA) filter, an ultra-low penetration air (ULPA) filter, a membrane filter, a nano-fiber filter, a carbon filter, a gas filter, a catalyst filter, or an anti-microbial filter. Moreover, the filter may be treated with chemical to remove certain gas or particles. Alternatively, the functional component 211 may be an ultraviolet air purifier with an ultraviolet light source to terminate a living organism. Alternatively, the functional component 211 may be an ozone generator, which produces a high concentration of ozone. Alternatively, the functional component 211 may be an impactor, which can help collecting particles. Alternatively, the functional component 211 may be a cyclone, which can help collecting particles. Alternatively, the functional component 211 may be another ionizer, which produces a high concentration of charged ions which help deposition of air pollutants distributed in extracted air. The functional component 211 is not limited to the aforementioned components, and may be a combination thereof. With the functional component 211, extracted air can be cleaned before recirculating back to room air.

The power supply 22 is connected to the operating tool 11, the ionizer 12, and/or the airflow device 13 via a power cable 32 between the operating device 10 and the electrical power box 20. In other words, units may utilize their own dedicated power supplies, such as mains or batteries, or share the power supply 22.

Typically, there is a controller 221 configured to control an ion generation rate of the ionizer, an airflow rate of the airflow generator, a power output of the power supply, or a deposition surface charge density of a deposition surface 40 as will be discussed in the following description. In this embodiment, the controller 221 is arranged in the power supply. However, in other embodiments, the controller 221 may be arranged in the airflow generator 21, in anywhere of the electrical power box 20, or out of the electrical power box 20. Optionally or preferably, the controller 221 is configured to be controlled locally or remotely by a computer (not shown), a tablet (not shown), a plate panel (not shown), a smart phone (not shown), or a remote controller (not shown).

The electronic apparatus capable of air pollution reduction 1 may further include a deposition surface 40, optionally or preferably located near the ionizer 12. The deposition surface 40 is adapted to capture particles charged by the charged ions emitted from the ionizer 12. The deposition surface 40 may have charges opposite to the charged ions. In this embodiment, the charges are provided by the power supply 22 via a power line 33. However, in other embodiments, the deposition surface 40 may be a self-powered object, which is standalone from the power supply 22. A charge density of the deposition surface 40 determines air pollutants deposition efficiency, and higher deposition efficiency indicates more air pollution reduction. Alternatively, the deposition surface 40 may be formed of uncharged material adapted to capture particles charged by the charged ions, for example, an electrostatic material.

Figure 1B:
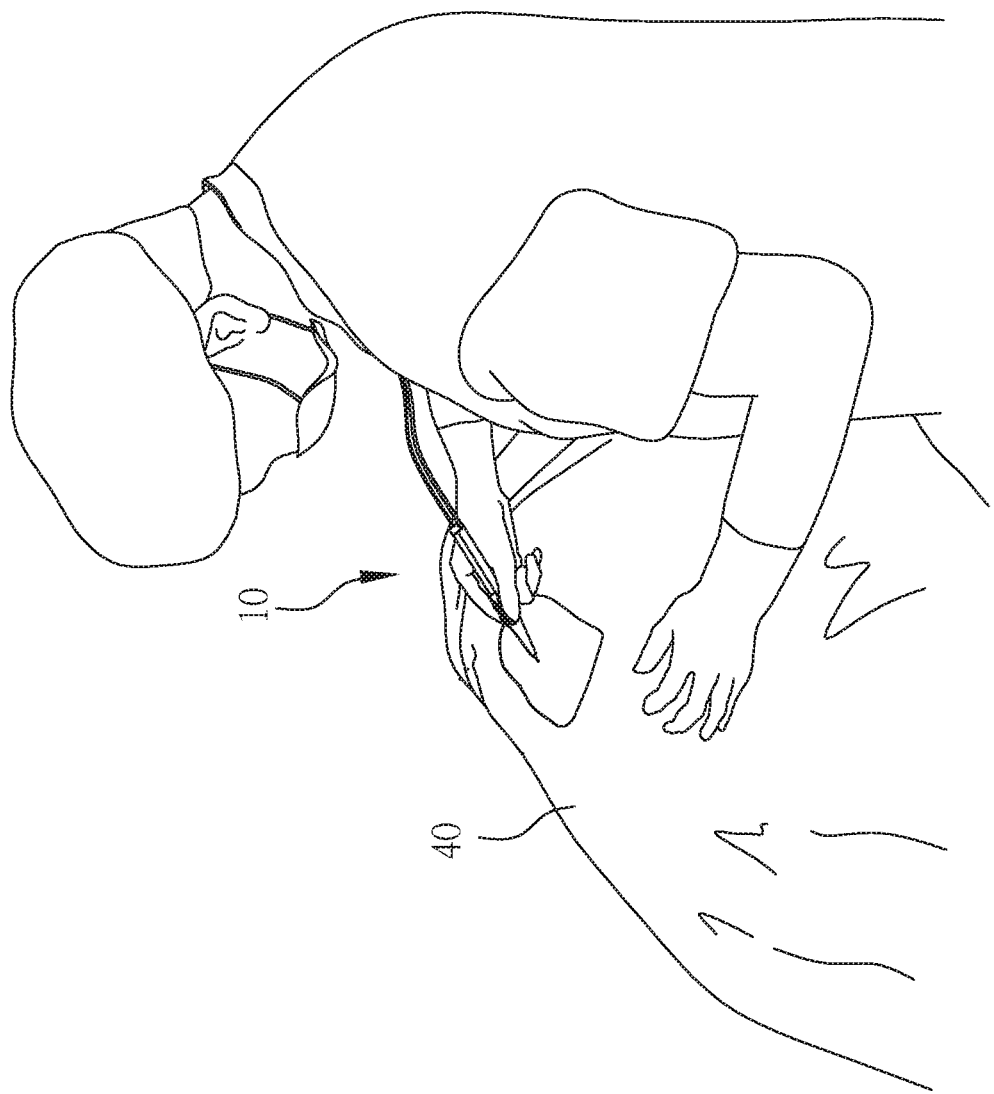
FIG. 1B is schematic diagram illustrating the deposition surface made into a piece of cloth or patient clothing according to the first embodiment of the present invention.

In some cases, the deposition surface 40 may be made into a piece of cloth or patient clothing as shown in FIG. 1B.

Optionally or preferably, there is an air pollution sensor 51 located adjacent to the operating tool 11. The air pollution sensor 51 is configured to detect an air pollution concentration, and send, according to its detection, a control signal to the controller 221 to control any or all of an airflow rate of the airflow generator 21, a power output to the operating tool 11, a power supplied to the ionizer 12, or the deposition surface charge density of the deposition surface 40.

Optionally or preferably, there is a sensor (or a switch) 52 configured to detect an operation of the operating tool 21, and generate a control signal to turn on the airflow device 13.

The sensor (or the switch) 52 may be arranged on the power cable 32 to monitor the operation of the operating tool 21 according to an electrical current flowing through the power cable 32.

According to experiment results, the electronic apparatus capable of air pollution reduction 1 of the present invention can reduce at least 50% of the concentration of the air pollution.

In particular, the experiment results show that adding the ionizer 12 alone reduces the total particle concentration by at least 64% at the particle source. This indicates that adding the ionizer 12 to the electrosurgical pencil helps reducing the particle concentration. The present invention can reduce the particle exposure and thus benefit the health of medical staff.

Second Embodiment

Figure 2:
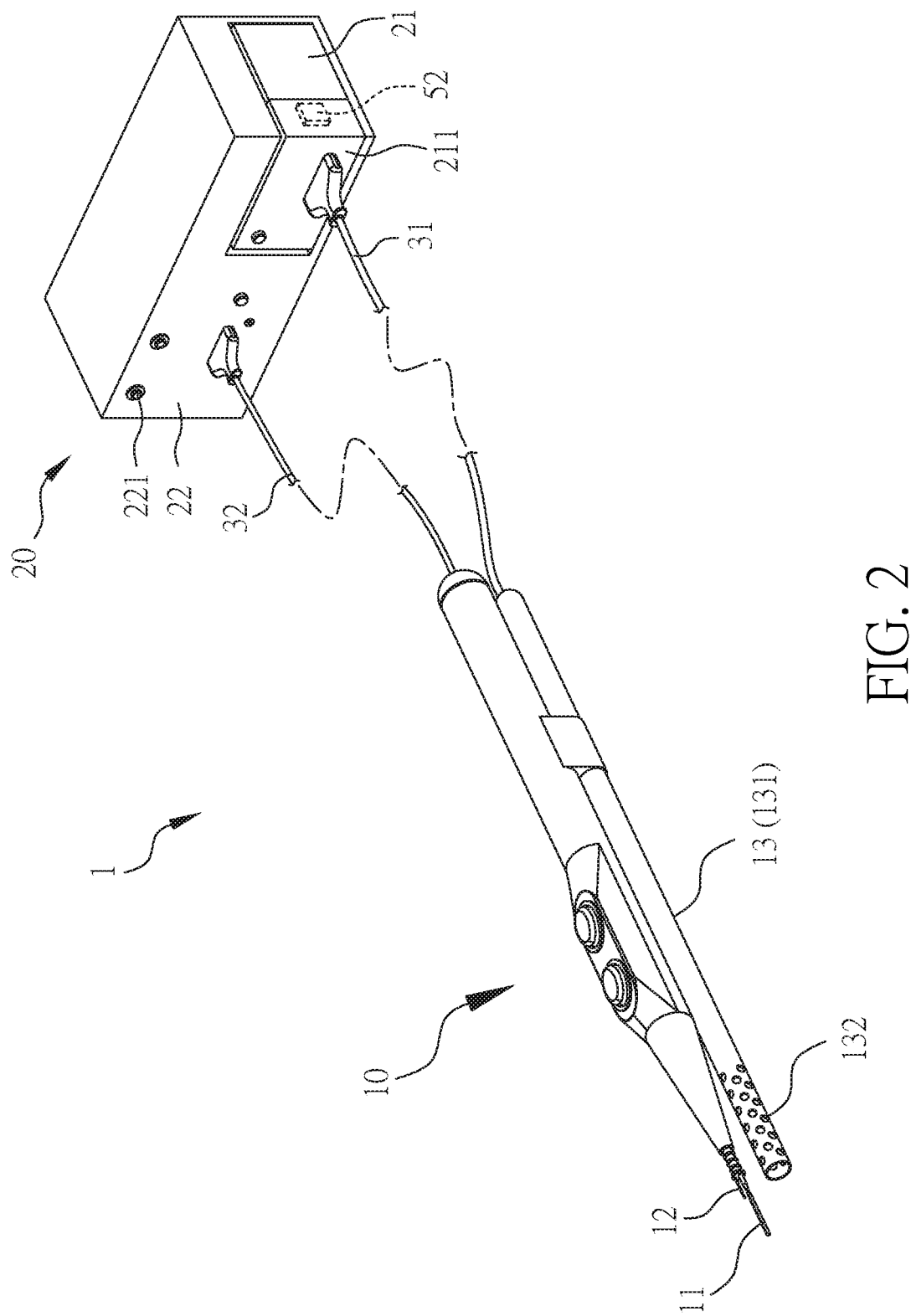
FIG. 2 is a schematic diagram illustrating the structure of the electronic apparatus capable of air pollution reduction according to a second embodiment of the present invention.

FIG. 2 is a schematic diagram illustrating the structure of the electronic apparatus capable of air pollution reduction 1 according to a second embodiment of the present invention.

The second embodiment is a variant of the first embodiment. The same or similar elements and their functions are referred to those in the first embodiment. The second embodiment differs from the first embodiment based on the structure and the location of the airflow device 13.

In this embodiment, the airflow device 13 does not wrap around the operating tool 11. Moreover, the airflow device 13 is disjointed from the operating tool 11, but it is still attached to the operating tool 11. The airflow device 13 is a removable body which can be easily fixed to and removed from the operating tool 11. However, in other embodiments, the airflow device 13 may be integrated with and attached to the operating tool 11, and thus form an irremovable body.

Figure 2A:
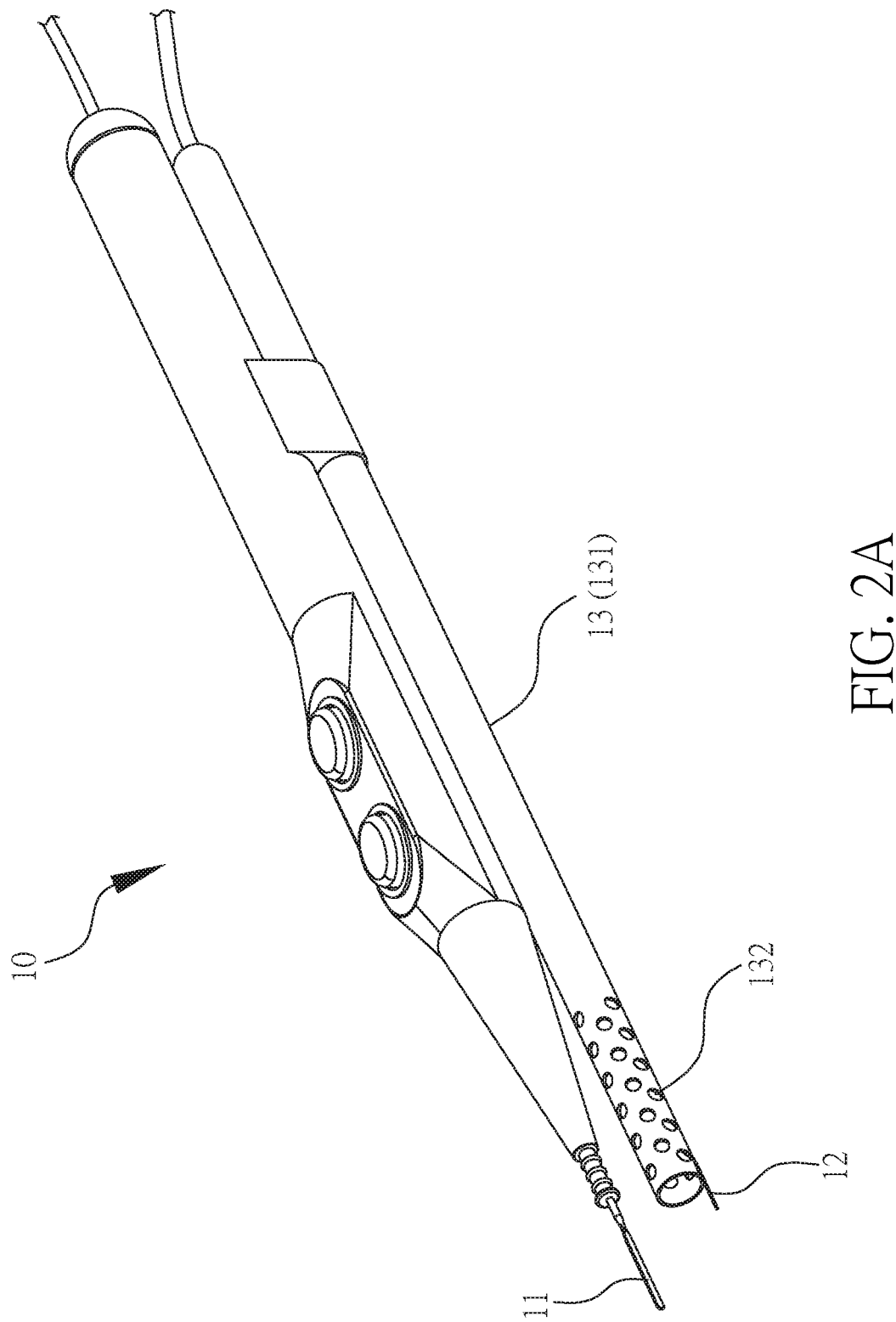
FIG. 2A shows a variant of the second embodiment.

FIG. 2A shows a variant of the second embodiment, wherein the ionizer 12 is embedded with the airflow device 13 rather than the operating tool 11, and it is arranged out of the airflow device 13, but in other embodiments, it may be arranged in the airflow device 13.

Third Embodiment

Figure 3:
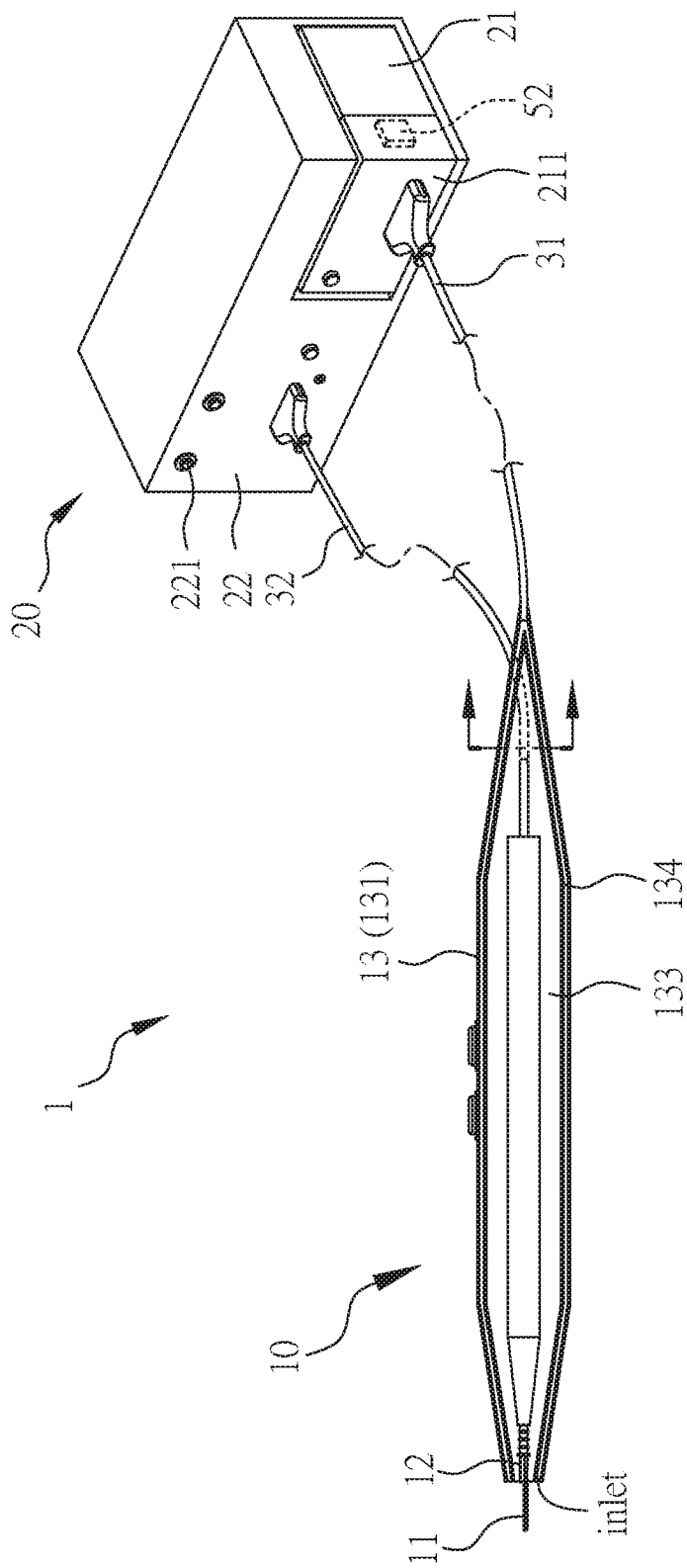
FIG. 3 is a schematic diagram illustrating the structure of the electronic apparatus capable of air pollution reduction according to a third embodiment of the present invention.

FIG. 3 is a schematic diagram illustrating the structure of the electronic apparatus capable of air pollution reduction 1 according to a third embodiment of the present invention;

The third embodiment is a variant of the first embodiment. The same or similar elements and their functions are referred to those in the first embodiment. The third embodiment differs from the first embodiment based on the structure of the airflow device 13.

In this embodiment, the shell 131 of the airflow device 13 wraps around the operating tool 11. The shell 131 holds the operating tool 11, but it is disjointed from the operating tool 11. The shell 131 is a removable body which can be easily fixed to and removed from the operating tool 11.

As shown in FIG. 3, the shell 131 is tubular. The shell 131 includes a plurality of layers to form an innermost region (or an inner tube) 133 and an outermost region (or an outer tube) 134. In this embodiment, the layers are concentric, and the outermost region 134 wraps around and isolated to the innermost region 133, but not limited thereto. The operating tool 11 is located in the innermost region 133. An air channel is formed in the outermost region 134, which is further connected to the air pipe 31, as shown in FIG. 3A.

Figure 3A:
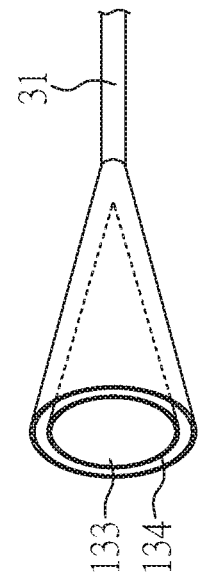
FIG. 3A is a schematic diagram illustrating a terminal portion of the innermost region and the outermost region of the shell according to the third embodiment of the present invention.

FIG. 3A is a schematic diagram illustrating a terminal portion of the innermost region 133 and the outermost region 134 of the shell 13 according to the third embodiment of the present invention.

The innermost region 133 appears as a cone, which converges from a larger circle to a smaller circle (almost a point) along a longitudinal axis (not shown) of the shell 131, and there is a wall (not labeled) at the end of the innermost region 133, so that air cannot flow into the air pipe 31. The outermost region 134 appears as a ring, which converges from a larger ring to a smaller ring adapted to be connected to the air pipe 31, so that the air channel can be formed therebetween.

It should be noted that the shell 131 does not have a plurality of opening holes 132 distributed thereon, and it only has an inlet for air to flow in or out.

Fourth Embodiment

FIGS. 4 and 4A are schematic diagrams illustrating the structure of the electronic apparatus capable of air pollution reduction 1 according to a fourth embodiment of the present invention.

The fourth embodiment is a variant of the first and the third embodiments. The same or similar elements and their functions are referred to those in the first and the third embodiments. The fourth embodiment differs from the first and the third embodiments based on the structure of the airflow device 13.

Similar to FIG. 3, as shown in FIGS. 4 and 4A, the shell 131 also includes an innermost region 133 and an outermost region 134. However, the shell 131 further includes a plurality of opening holes 132 distributed near an inlet of the shell 131. Optionally or preferably, a line L divides the shell 131 (and thus the airflow device 13) into a former portion and a latter portion, the former portion has large opening holes 132, and the latter portion having small opening holes 132.

Typically, the shell 131 may have additional openings 136 for buttons, wires or other components to pass through.

Fifth Embodiment

FIG. 5 is a schematic diagram illustrating the structure of the electronic apparatus capable of air pollution reduction according to a fifth embodiment of the present invention.

The fifth embodiment is a variant of the first and the third embodiments. The same or similar elements and their functions are referred to those in the first and the third embodiments. The fifth embodiment differs from the first and the third embodiments based on the structure of the airflow device 13.

FIGS. 5A to 5C are schematic diagram illustrating the structure of the shell according to the fifth embodiment of the present invention.

Similar to FIG. 3, as shown in FIGS. 5 and 5A to 5C, the shell 131 also includes an innermost region 133 and an outermost region 134. However, the shell 131 further includes a plurality of opening holes 132 distributed near an inlet of the shell 131. Moreover, the outermost region 134 of the shell 131 of the airflow device includes a plurality of radial subsections 137 isolated to each other, and each radial subsection 137 has a group of opening holes 132. Furthermore, as shown in FIGS. 5A to 5C, one group of opening holes 132a (only one of three opening holes 132a is illustratively labeled for clarity) is located before another group of opening holes 132b (only one of three opening holes 132b is illustratively labeled for clarity) along a longitudinal axis (not shown) of the shell 131. In such distribution, former opening holes 132a can be used to capture air pollutants upstream of the airflow, and latter opening holes 132b can be used to capture air pollutants downstream of the airflow. Such distribution of opening holes 132 can avoid air pollutants enter into former opening holes 132 but escape from latter opening holes 132. Herein, the term "former" means near the tip of the operating tool 11, and the term "latter" means far from the tip of the operating tool 11.

It is to be understood that the subsections 137 may have different sizes, shapes, and distributions, and each subsection 137 has a group of opening holes 132 used to capture air pollutants flowing through its location.

As shown in FIGS. 5B and 5C, at least one of the radial subsections 137 has a sealed portion 137c disconnected to the airflow generator 21, and located before the opening holes 132b along the longitudinal axis of the shell 131, because no air channel is needed before the opening holes 132b, and the sealed portion 137c avoids air to flow back to the inlet of the shell 131.

In fact, the opening holes 132 may be distributed on the shell 131 at suitable places to pursue more efficiency of air pollution reduction, and the distribution may be calculated by fluid mechanics.

Typically, the shell 131 may have additional openings 136 for buttons, wires or other components to pass through.

Sixth Embodiment

FIG. 6 is a schematic diagram illustrating the structure of the electronic apparatus capable of air pollution reduction 1 according to a sixth embodiment of the present invention.

The sixth embodiment is a variant of the first embodiment. The same or similar elements and their functions are referred to those in the first embodiment. The sixth embodiment differs from the first embodiment based on the operating tool 11, which is a dental drill in this embodiment.

Similarly, the airflow device 13 is located adjacent to the dental drill, and the shell 131 of the airflow device 13 have a plurality of opening holes 132 distributed thereon for air to flow in or out. The shell 13 may be an irremovable body wrapping around and integrated with the dental drill, a removable body wrapping around the dental drill, or a removable body fixed to the dental drill, without modifying the structure of the dental drill.

As previously mentioned, the operating tool 11 may be an electrosurgical pencil, an electrocautery, a laser surgical device, a dental drill, dental scalar tool, a prophy angle, or a welding torch, and is not limited thereto. A person skill in the art may combine the aforementioned operating tool 11 with the airflow device 13, so that the embodiments and the corresponding drawings for the aforementioned operating tool 11 other than the electrosurgical pencil and the dental drill are deemed not necessary.

Although the present invention has been explained in relation to its preferred embodiment, it is to be understood that many other possible modifications and variations can be made without departing from the spirit and scope of the invention as hereinafter claimed.

What is claimed is:

1. An electronic apparatus capable of air pollution reduction, comprising:
    an operating tool; and
    an airflow device located adjacent to the operating tool, and having a shell with one or more opening holes distributed thereon for air to flow in or out, wherein air pollution is generated during an operation of the operating tool.

2. The electronic apparatus capable of air pollution reduction of claim 1, wherein the operating tool is a hand-held tool or a machine-held tool.

3. The electronic apparatus capable of air pollution reduction of claim 1, wherein the operating tool is an electrosurgical pencil, a electrocautery, a laser surgical device, a dental drill, dental scalar tool, a prophy angle, a welding torch, or an air pollution generating device.

4. The electronic apparatus capable of air pollution reduction of claim 1, further comprising an ionizer located adjacent to the operating tool, and configured to emit charged ions, wherein the ionizer includes at least one point ionizer, at least one wire, and/or at least one ground plate.

5. The electronic apparatus capable of air pollution reduction of claim 4, further comprising an airflow generator connected to the airflow device, wherein the airflow generator is a vacuum pump configured to extract air from the airflow device, or an air blower configured to blow air into the airflow device.

6. The electronic apparatus capable of air pollution reduction of claim 5, wherein the airflow generator is equipped with
    (i) a high efficiency particulate air (HEPA) filter, an ultra-low penetration air (ULPA) filter, a membrane filter, a nano-fiber filter, a carbon filter, a gas filter, a catalyst filter, or an anti-microbial filter; or
    (ii) an ultraviolet air purifier with an ultraviolet light source to terminate a living organism;
    (iii) an ozone generator;
    (iv) an impactor; and/or
    (v) a cyclone.

7. The electronic apparatus capable of air pollution reduction of claim 1, further comprising a deposition surface having charges opposite to the charged ions.

8. The electronic apparatus capable of air pollution reduction of claim 1, further comprising a deposition surface formed of uncharged material adapted to capture particles charged by the charged ions.

9. The electronic apparatus capable of air pollution reduction of claim 5, further comprising a power supply connected to the operating tool, the ionizer, and/or the airflow device.

10. The electronic apparatus capable of air pollution reduction of claim 9, wherein the airflow generator and the power supply are integrated into an electrical power box.

11. The electronic apparatus capable of air pollution reduction of claim 9, further comprising a controller configured to control an ion generation rate of the ionizer, an airflow rate of the airflow generator, a power output of the power supply, or a deposition surface charge density of a deposition surface.

12. The electronic apparatus capable of air pollution reduction of claim 11, wherein the controller is configured to be controlled by a computer, a tablet, a plate panel, a smart phone, or a remote controller.

13. The electronic apparatus capable of air pollution reduction of claim 1, wherein the shell of the airflow device is
    (i) an irremovable body wrapping around and integrated with the operating tool; or
    (ii) a removable body wrapping around the operating tool; or
    (iii) a removable body fixed to the operating tool.

14. The electronic apparatus capable of air pollution reduction of claim 1, wherein the shell of the airflow device includes a plurality of layers to form an innermost region and an outermost region wrapping around and isolated to the innermost region, the operating tool is located in the innermost region, and an air channel is formed in the outermost region.

15. The electronic apparatus capable of air pollution reduction of claim 5, wherein the shell of the airflow device includes a plurality of radial subsections isolated to each other, each radial subsection has a group of opening holes, and one group of opening holes is located before another group of opening holes along a longitudinal axis of the shell.

16. The electronic apparatus capable of air pollution reduction of claim 15, wherein at least one of the radial subsections has a sealed portion disconnected to the airflow generator, and located before the opening holes along the longitudinal axis of the shell.

17. The electronic apparatus capable of air pollution reduction of claim 1, wherein the shell of the airflow device includes a former portion having large opening holes, and a latter portion having small opening holes.

18. The electronic apparatus capable of air pollution reduction of claim 5, further comprising an air pollution sensor located adjacent to the operating tool, configured to detect an air pollution concentration, and send a control signal to control any or all of an airflow rate of the airflow generator, a power output to the operating tool, a power supplied to the ionizer, or a deposition surface charge density of a deposition surface.

19. The electronic apparatus capable of air pollution reduction of claim 1, further comprising a sensor or a switch configured to detect an operation of the operating tool, and generate a control signal to turn on the airflow device, an ionizer, and/or a deposition surface.

* * * * *